United States Patent
Masuda et al.

(10) Patent No.: US 6,187,783 B1
(45) Date of Patent: Feb. 13, 2001

(54) PHENANTHRIDINIUM DERIVATIVES

(75) Inventors: Akira Masuda, Yono; Masato Suwa, Gunma; Masanobu Suzuki, Omiya, all of (JP)

(73) Assignee: Nippon Kayaku Kabushiki Kaisha, Tokyo (JP)

( * ) Notice: Under 35 U.S.C. 154(b), the term of this patent shall be extended for 0 days.

(21) Appl. No.: 09/308,516

(22) PCT Filed: Nov. 21, 1997

(86) PCT No.: PCT/JP97/04252
 § 371 Date: May 20, 1999
 § 102(e) Date: May 20, 1999

(87) PCT Pub. No.: WO98/23614
 PCT Pub. Date: Jun. 4, 1998

(30) Foreign Application Priority Data

Nov. 25, 1996 (JP) ................................................ 8-328039

(51) Int. Cl.$^7$ ..................... A61K 31/435; C07D 491/00; C07D 471/00
(52) U.S. Cl. .............................. 514/279; 546/41; 546/42; 546/45; 546/50; 546/51; 546/58; 514/280; 514/283
(58) Field of Search ..................... 514/279, 280, 514/283; 546/38, 41, 42, 58, 48, 50, 51

(56) References Cited

U.S. PATENT DOCUMENTS 5,747,502 * 5/1998 Hanaoka et al. .................... 514/280

FOREIGN PATENT DOCUMENTS 86979.91 9/1993 (AU) .
0 432 630 6/1991 (EP) .

* cited by examiner

*Primary Examiner*—Charanjit S. Aulakh
(74) *Attorney, Agent, or Firm*—Nields, Lemack & Dingman

(57) ABSTRACT

A novel phenanthridinium derivative represented by general formula (A):

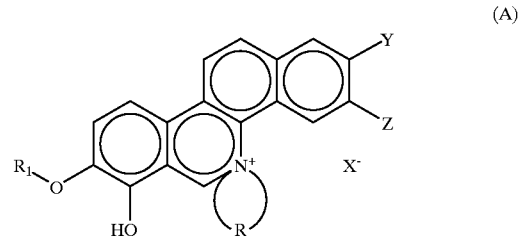

wherein $R_1$ is a substituted or unsubstituted lower aliphatic hydrocarbon group; R is an aliphatic hydrocarbon chain having 2 to 6 carbon atoms which may optionally be substituted with a substituent selected from the group consisting of a lower alkyl group, a halogen and a hydroxy group; each of Y and Z independently represents a hydrogen, a hydroxy or a lower alkoxy group; or Y and Z are combined together to form methylenedioxy or a phenyl ring;

and, $X^-$ is an acid residue or a hydrogen acid residue, exhibits an antitumor activity and has resistance to chemical reduction as well as biological metabolic reactions and is thus advantageous for use as a medicine.

7 Claims, No Drawings

PHENANTHRIDINIUM DERIVATIVES

This application is a 371 of PCT/JP97/04252, filed Nov. 21, 1997, now WO 98/23614 published Apr. 06, 1998.

FIELD OF THE INVENTION

The present invention relates to a novel phenanthridinium derivative which has an antitumor activity and is expected to be effective as a medicine, and pharmaceutical use thereof.

BACKGROUND ART

Alkylating agents, metabolic antagonists, antibiotics, plant alkaloids, etc. are currently used in chemotherapy for patients with cancer.

2,3-(Methylenedioxy)-5-methyl-7-hydroxy-8-methoxy-benzo[c]phenanthridinium chloride or iodide reported in Chem. Pharm. Bull., 33, 1763 is known to exhibit an antitumor activity (Japanese Patent KOKAI Nos. 2-243628 and 3-184916). Benzo[c]phenanthridinium derivertive and its antitumor activity are also reported in Japanese Patent KOKAI No. 5-208959.

Malignant tumor has a diversity of characteristics. Moreover, use of these antitumor agents causes resistance thereto. It is thus desired to develop a new antitumor agent.

DISCLOSURE OF THE INVENTION

The present inventors have found a novel phenanthridinium derivative having a structure formed by linking the nitrogen atom at the 5-position with the carbon atom at the 6-position through aliphatic hydrocarbon chains adjacent thereto and also found that the new phenanthridinium derivative exhibits an antitumor activity and is resistant to chemical reduction and to biological metabolic reactions. These properties of the phenanthridinium derivative are found to be extremely advantageous for applying the same to a medicine, and the present invention was accomplished thereby.

That is, the present invention relates to a novel phenanthridinium derivative represented by general formula (A):

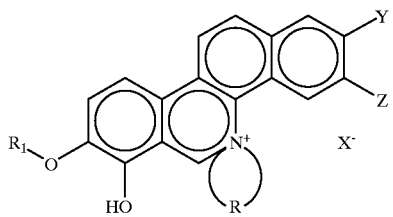

(A)

wherein
  $R_1$ is a substituted or unsubstituted lower aliphatic hydrocarbon group;
  R is an aliphatic hydrocarbon chain having 2 to 6 carbon atoms which may optionally be substituted with a substituent selected from the group consisting of a lower alkyl group, a halogen and a hydroxy group;
  each of Y and Z independently represents a hydrogen, a hydroxy or a lower alkoxy group; or Y and Z are combined together to form methylenedioxy or a phenyl ring; and,
  $X^-$ is an acid residue or a hydrogen acid residue.

The present invention further relates to a novel phenanthridinium derivative represented by general formula (B):

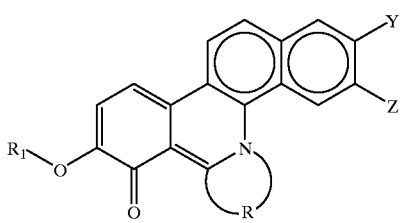

(B)

wherein
  $R_1$ is a substituted or unsubstituted lower aliphatic hydrocarbon group;
  R is a lower aliphatic hydrocarbon chain having 2 to 6 carbon atoms which may optionally be substituted with a substituent selected from the group consisting of a lower alkyl group, a halogen and hydroxy group;
  each of Y and Z independently represents a hydrogen, a hydroxy or a lower alkoxy group; or Y and Z are combined together to form methylenedioxy or a phenyl ring.

The present invention further relates to a pharmaceutical composition comprising as an active ingredient the compound represented by general formula (A) or (B) together with a pharmacologically acceptable carrier.

The present invention further relates to an antitumor agent comprising as an active ingredient the compound represented by general formula (A) or (B) together with a pharmacologically acceptable carrier.

The present invention further relates to the compound represented by general formula (A) or (B) for use in the pharmaceutical composition as an active ingredient.

The present invention further relates to use of the compound represented by general formula (A) or (B) in the production of a pharmaceutical composition for the treatment or prevention of tumor.

The present invention further relates to a method for the treatment or prevention of tumor which comprises administering to human the compound represented by general formula (A) or (B) at an effective dose.

BEST MODE FOR CARRYING OUT THE INVENTION

In general formulas (A) and (B) in the present invention, the lower aliphatic hydrocarbon group includes for example an alkyl group having 1 to 5 carbon atoms and an alkenylmethyl group having 3 to 5 carbon atoms. Examples of such an alkyl group having 1 to 5 carbon atoms are methyl, ethyl, propyl, isopropyl, n-butyl, t-butyl, etc. Examples of the alkenylmethyl group having 3 to 5 carbon atoms are allyl, 2-butenyl, 3-methyl-2-butenyl, etc. These lower aliphatic hydrocarbon groups may optionally be substituted, and examples of such substituents are a hydroxy group, a $C_1$–$C_5$ alkoxy group, a $C_1$–$C_5$ alkoxycarbonyl group, an acetyl group, a halogen, a carbamoyl group or a phenyl group optionally substituted with a methoxy group.

Specific examples of the aliphatic hydrocarbon group which may be substituted or unsubstituted are methyl, ethyl, propyl, isopropyl, 2-hydroxyethyl, 2-methoxyethyl, 2-acetoxyethyl, 2-hydroxypropyl, allyl, 2-butenyl, 3-methyl-2-butenyl, methoxycarbonylmethyl, isopropoxycarbonylmethyl, carbamoylmethyl, benzyl, 4-methoxyphenylmethyl, fluoromethyl, trifluoromethyl, etc. Particularly preferred are methyl, ethyl, allyl, 2-hydroxyethyl, 2-methoxyethyl, 2-acetoxyethyl, carbamoylmethyl and trifluoromethyl.

The aliphatic hydrocarbon chain having 2 to 6 carbon atoms in general formulas (A) and (B) of the present invention, which may be substituted with a substituent selected from the group consisting of a lower alkyl group, a halogen and a hydroxy group, refers to, e.g., a substituted or unsubstituted polymethylene group having 2 to 6 carbon atoms. The lower alkyl group as the substituent of the aliphatic hydrocarbon chain is a alkyl group having 1 to 5 carbon atoms which is exemplified by methyl, ethyl, propyl, i-propyl, butyl, t-butyl, pentyl, etc. Preferred examples of the substituent are methyl and ethyl. Examples of the halogen atom are fluorine, chlorine, bromine and iodine.

Specifically, the aliphatic hydrocarbon chain having 2 to 6 carbon atoms, which may be substituted or unsubstituted, refers to —$CH_2CH_2$—, —$CH_2CH_2CH_2$—, —$CH_2CH(CH_3)CH_2$—, —$CH_2C(CH_3)_2CH_2$—, —$CH_2CH(OH)CH_2$—, —$CH_2CHFCH_2$—, —$CH_2CF_2CH_2$—, —$CH_2CHClCH_2$—, —$CH_2CH_2CH_2CH_2$—, —$CH_2CH_2CH_2CH_2CH_2$—, —$CH_2CH_2CH_2CH_2CH_2CH_2$—, etc. Particularly preferred is an unsubstituted polymethylene chain having carbon atoms 3 to 4, such as —$CH_2CH_2CH_2$— or —$CH_2CH_2CH_2CH_2$—.

In general formulas (A) and (B) of the present invention, examples of the lower alkoxy group is an alkoxy group having 1 to 5 carbon atoms such as methoxy, ethoxy, n-propoxy, i-propoxy, n-butoxy, i-butoxy, t-butoxy, pentoxy, etc., preferably an alkoxy group having 1 to 3 carbon atoms such as methoxy, ethoxy, n-propoxy or i-propoxy.

The acid residue of $X^-$ in general formula (A) of the present invention means an acid residue that forms a normal salt, e.g., $X^-$ is a halogen ion such as a chloride, bromide, iodide or fluoride ion, or a sulfate, nitrate or p-toluenesulfonate ion. The hydrogen acid residue means an acid reside that forms a hydrogen acid salt. The hydrogen acid residue contains 1 or 2 hydrogen atoms and is exemplified by a hydrogensulfate ion, a dihydrogenphosphate ion, etc. Among them, a chloride ion and a hydrogensulfate ion are particularly preferred.

In the present invention, preferred examples of the compounds are those of general formulas (A) and (B) wherein $R^1$ is methyl, ethyl, allyl, 2-hydroxyethyl, 2-methoxyethyl, 2-acetoxyethyl, carbamoylmethyl or trifluoromethyl, R is an unsubstituted polymethylene chain having 3 to 4 carbon atoms, and Y and Z are combined together to represent methylenedioxy or to form a phenyl ring.

The compounds represented by general formula (A) may be prepared by the following processes, which are classified into two types. Each process is explained below.

1. Synthesis of the compound represented by general formula (A) wherein $R_1$ represents methyl (hereinafter referred to as synthesis of type 1 in general formula (A)):

(a) The compound of general formula (A) wherein $R_1$ is methyl can be synthesized by the following reaction scheme 1.

Reaction scheme 1:

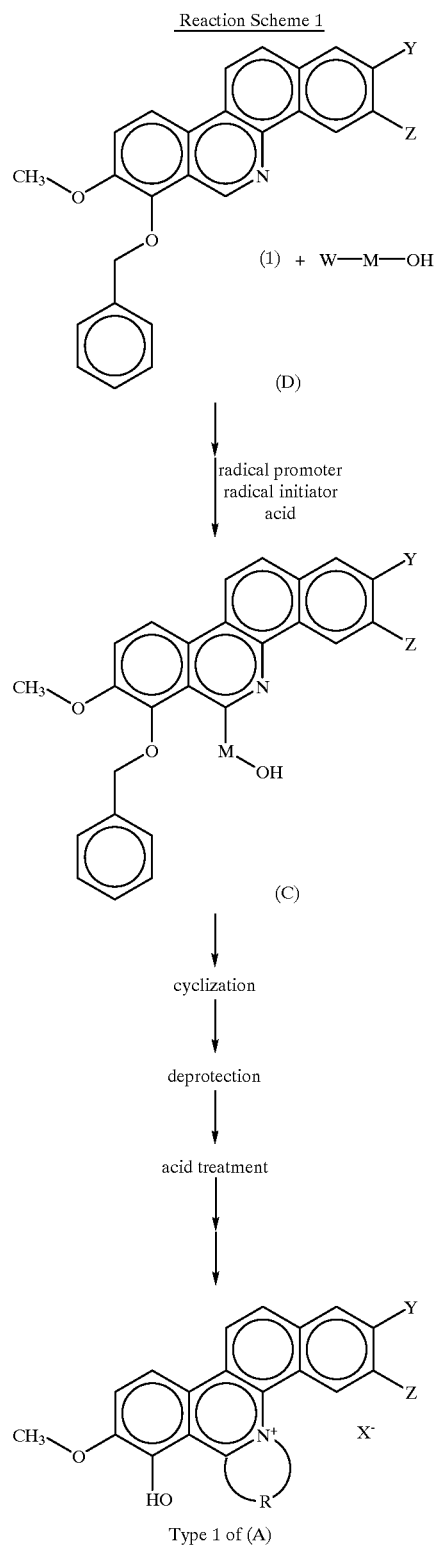

In the starting compounds of general formula (1), Y and Z have the same significance as defined in general formulas (A) and (B). The starting compound of general formula (1) wherein each of Y and Z represents independently a hydrogen, a hydroxy or a lower alkoxy group, or Y and Z are combined together to form methylenedioxy, i.e., 7-benzyloxy-8-methoxy-benzo[c]phenanthridine derivatives, may be synthesized by the process described in Japanese Patent KOKAI No. 5-208959.

The starting compound of general formula (1) wherein Y and Z are combined together to form a phenyl ring, i.e., 8-benzyloxy-9-methoxy-naphtho[2,3-c]phenanthridine derivative may be synthesized by reaction scheme 3 later described.

In general formula (D), M corresponds to R in general formulas (A) and (B) and represents an aliphatic hydrocarbon chain having 2 to 6 carbon atoms which may optionally be substituted with a substituent selected from the group consisting of a lower alkyl group, a halogen and a hydroxy group; and W represents iodine or bromine.

The alkyl halide compound of general formula (D) may be synthesized in a conventional manner.

The compound shown by formula (C) may be prepared by heating the compound of general formula (1) and the alkyl halide compound of general formula (D) in a solvent such as acetonitrile, etc. in the presence of a radical promoter such as an organotin hydride, organosilane hydride, etc.; a radical initiator such as 2,2'-azobis(isobutyronitrile), etc.; and an acid such as trifluoroacetic acid, while stirring.

The compound of general formula (C) is reacted with an acid chloride such as methanesulfonyl chloride, p-toluenesulfonyl chloride, etc. or an acid anhydride such as trifluoroacetic anhydride, etc. in an organic solvent in the presence of a base such as triethylamine, etc. under ice cooling to room temperature, followed by treating the reaction mixture at room temperature to 100° C. for cyclization.

Subsequently, deprotection of the reaction product is carried out, preferably without isolating and purifying the product. The deprotection as used herein refers to removing benzyl group at the 7-position in general formula (C) off.

The removal of 7-benzyl group may be effected by treating at room temperature to 100° C. under an acidic condition using conc. hydrochloric acid, etc.

The acid treatment is carried out by dissolving in a solvent the compound resulting from deprotection, and adding an acid, e.g., hydrochloric acid, sulfuric acid, p-toluenesulfonic acid, etc. to the solution. In general, the amount of the acid is approximately 1 to 3 mols per mol of the compound.

Following the procedures above, the compound of type 1 represented by general formula (A) can be obtained.

(b) The compound of type 1 in general formula (A) may also be synthesized by the following reaction scheme 2.
Reaction scheme 2:

Reaction Scheme 2

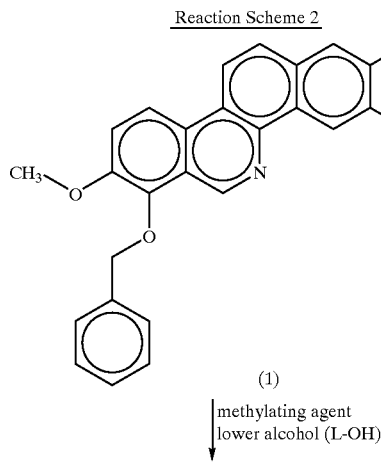

(1)

| methylating agent
| lower alcohol (L-OH)

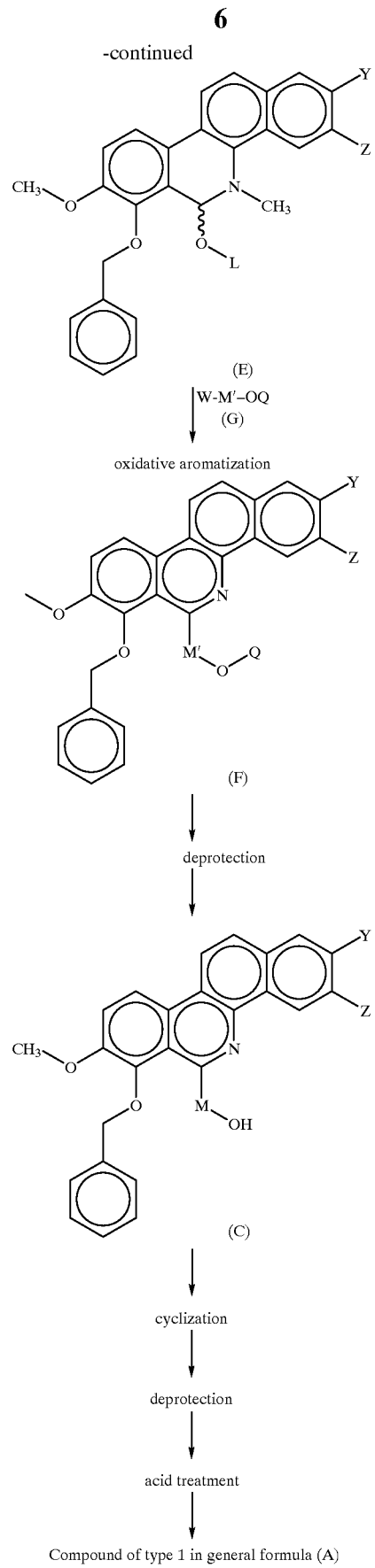

-continued (E)

| W-M'-OQ
(G)

oxidative aromatization (F)

deprotection (C)

cyclization deprotection acid treatment

Compound of type 1 in general formula (A)

In the reaction scheme above, W is an organic metal or an inorganic metal salt; L is a lower alkyl group; M' is a aliphatic hydrocarbon chain having 2 to 6 carbon atoms which may optionally be substituted with a substituent selected from the group consisting of a lower alkyl group, a halogen and a hydroxy group; and Q is a protective group.

The reaction of the compound of general formula (1) with a methylating agent is carried out with heating, in the absence of a solvent or by dissolving them in a $C_6$–$C_{10}$ hydrocarbon solvent such as toluene, xylene, etc. The reaction is carried out at a temperature generally between 50 to 180° C., preferably 100 to 150° C., generally for 1 to 24 hours, preferably for 2 to 10 hours.

Any methylating agent may be employed so long as it is generally used for N-methylation of a pyridine ring. Methyl sulfonate, used for methylation of, e.g., a methyl substituted-benzenesulfonate, or a methyl trihalogenomethanesulfonate is preferred. Specific examples include methyl p-toluenesulfonate, methyl 2-nitorobenzenesulfonate and methyl trifluoromethanesulfonate.

The thus N-methylated compound is mixed with a lower alcohol (L—OH) such as ethanol, etc., preferably methanol, ethanol or n-propanol, generally at 0° C. to room temperature in the presence of a base to give the compound of general formula (E).

The compound represented by general formula (E) is dissolved in an aprotic solvent, e.g., a hydrocarbon solvent such as benzene, toluene, xylene, etc.; an ethereal solvent such as diethyl ether, diisopropyl ether, 1,2-dimethoxyethane, tetrahydrofuran, etc.; a halogen type solvent such as methylene chloride, 1,2-dichloroethane, etc. The organic metal compound of general formula (G) is then added to the solution of the compound (E) in 1 to 10 equimolar amount, preferably 1 to 3 equimolar amount and if necessary, a reaction accelerator such as a boron trifluoride-ether complex, titanium tetraisopropoxide, etc. is added to the mixture. The reaction is carried out by stirring the mixture at −78 to 50° C., preferably −20° C. to room temperature, for 5 minutes to 24 hours, preferably 10 minutes to 10 hours.

The organic metal compound of general formula (G) may be any organic metal compound so long as it can be used for a conventional nucleophilic substitution reaction. As the organic metal compound, there are, for example, organic lithium, magnesium, zinc, aluminum or copper compounds, with particular preference of an organomagnesium compound. Specific examples of the organometal compound include 3-(t-butyldimethylsiloxy)propylmagnesium bromide, 2-methyl-3-(t-butyldimethylsiloxy) propylmagnesium bromide and 4-(t-butyldimethylsiloxy) butylmagnesium bromide.

The reaction product obtained through the nucleophilic substitution reaction described above is oxidatively aromatized with an oxidizing agent to give the compound of general formula (F). A variety of oxidizing agents such as manganese dioxide, lead tetraacetate and dichlorodicyanobenzoquinone (DDQ), preferably manganese dioxide, may be employed for the reaction. The reaction is carried out at 0 to 120° C., preferably room temperature to 100° C. for 1 to 120 minutes, preferably 5 to 60 minutes.

Deprotection from the compound of general formula (F) gives the compound of general formula (C). As the protective group, there are generally substituents used to protect a hydroxy group, e.g., a substituted methyl group such as methoxymethyl, benzyloxymethyl, tetrahydrofuryl, t-butyl, p-methoxybenzyl, triphenylmethyl, etc.; a trialkylsilyl group such as t-butyldimethylsilyl, trimethylsilyl, etc.; an acyl group such as acetyl, chloroacetyl, benzoyl, isobutyryl, etc. An appropriate procedure for each protective group is used to remove the protective group. For example, removal of a protective group Q and a trialkylsilyl type protective group used to protect a hydroxy group in M' is effected by adding to the reaction mixture a fluoride compound such as tetrabutylammonium fluoride, potassium fluoride, cesium fluoride, etc. in a solvent such as tetrahydrofuran, acetonitrile, etc. and maintaining at 0 to 80° C., preferably 0° C. to room temperature. Thereafter, the compound of general formula (C) is cyclized as in the reaction scheme 1. By removal of the protective group and then acid treatment, the objective compound of type 1 represented by general formula (A) can be synthesized.

(c) Among the compound of general formula (1) used as the starting compound in the reaction schemes 1 and 2, a 8-benzyloxy-9-methoxy-naphtho[2,3-c]phenanthridine derivative, wherein Y and Z are combined together to form a phenyl ring, may be synthesized according to reaction scheme 3.

Reaction scheme 3:

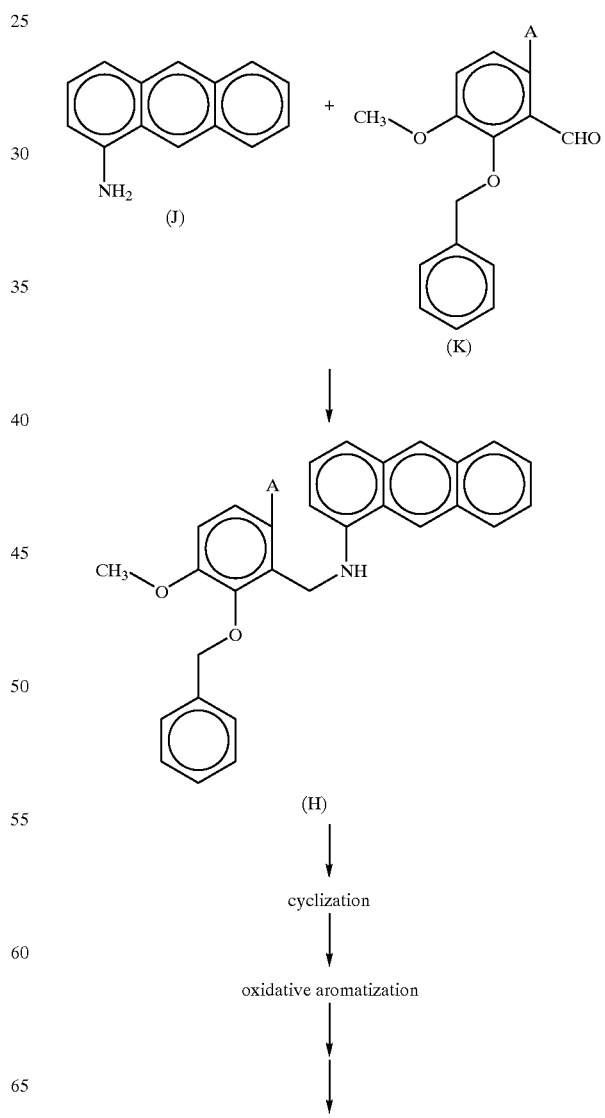

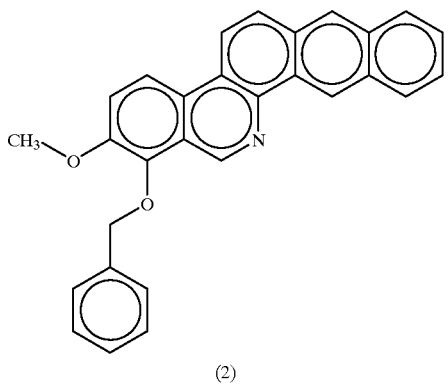

(2)

1-Aminoanthracene of formula (J) and a 2-benzyloxy-3-methoxy-6-halogenobenzaldehyde of formula (K), which may be obtained by the process described in, e.g., J. C. S. Perkin I, 1221 (1976) and J. Org. Chem., 53, 1708 (1988), are heated at 80 to 11° C. in toluene or benzene for 1 to 3 hours. The reaction mixture is concentrated and the water, co-product is removed by azeotropic distillation with toluene or benzene. Preferably, fresh toluene or benzene is added to the concentrate and the above procedure of heating followed by concentration is repeated 2 to 4 times to give the dehydrated condensation product (Schiff base) almost quantitatively. The condensed position of the dehydrated condensation product is reduced to give the compound of general formula (H).

Any reducing agent may be employed as far as it can reduce a carbon-nitrogen double bond. The reduction is preferably carried out at a reaction temperature of −10 to 40° C. using sodium cyanoborohydride or dimethylaminoboron.

In formulas (K) and (H), A represents a halogen atom.

The compound of general formula (H) is cyclized (condensation reaction via removal of a hydrogen halide) in an organic solvent using an organotin hydride compound, preferably a trihydrocarbon (1 to 8 carbon atoms) tin hydride compound such as tributyltin hydride or trioctyltin hydride, or a dihydrocarbon (1 to 8 carbon atoms) tin hydride compound, e.g., diphenyltin hydride. tributyltin hydride is generally preferably used as the organotin hydride compound in this reaction. The reaction may be carried out by dissolving the compound of general formula (H) and 1 to 6 equimolar amount, preferably 2 to 3 equimolar amount of the organotin hydride compound in an organic solvent, preferably a hydrocarbon solvent with 6 to 10 carbon atoms, e.g., toluene, xylene, benzene, etc., and heating the solution at 60 to 150° C., preferably 80 to 130° C. for 2 minutes to 4 hours, preferably 5 minutes to an hour, preferably in the presence of a radical initiator such as 2,2'-azobis (isobutyronitrile), 2,2'-azobis(2-methylbutyronitrile) or benzoyl peroxide, etc., thereby completing the cyclization.

Next, the reaction mixture, preferably without isolating the condensed product therefrom, is subjected to oxidative aromatization of the cyclized position with an oxidizing agent. The reaction is carried out at 0 to 120° C., preferably at room temperature to 100° C. for 1 to 120 minutes, preferably 5 to 60 minutes to give the 8 -benzyloxy-4-methoxy-naphtho[2,3-c]phenanthridine derivative represented by general formula (2). A variety of oxidizing agents may be employed for this reaction. Examples of the oxidizing agents are manganese dioxide, lead tetraacetate and dichlorodicyanobenzoquinone (DDQ), with manganese dioxide being particularly preferred.

2. Synthesis of the compound represented by general formula (A) wherein $R_1$ is a substituted or unsubstituted lower aliphatic hydrocarbon group other than methyl (hereinafter referred to as synthesis of type 2 in general formula (A)):

The compound of type 2 in general formula (A), wherein $R_1$ is a substituted or unsubstituted aliphatic hydrocarbon group other than methyl is shown by the following formula:

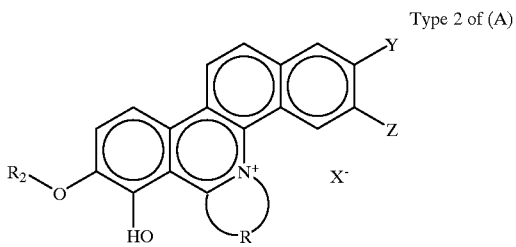

Type 2 of (A)

wherein $R_2$ is a substituted or unsubstituted aliphatic hydrocarbon group other than methyl; and R, Y, Z and $X^-$ have the same significance as defined in general formula (A). The compound of type 2 may be synthesized by the following procedures.

That is, the compound of general formula (3):

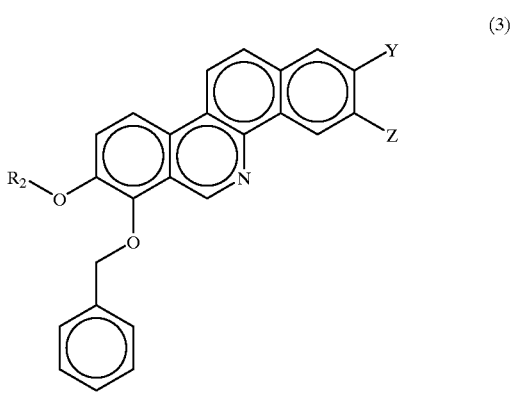

(3)

wherein $R_2$ is a substituted or unsubstituted aliphatic hydrocarbon group other than methyl; and Y and Z have the same significance as defined in general formula (A), is used as the starting compound. The reaction is carried out in a manner similar to the reaction scheme 1 or 2. That is, the compound of type 2 may be synthesized as in the reaction scheme 1 or 2 except that the compound of general formula (3) is used in place of the compound of general formula (1). Where a compound containing, e.g., hydroxy group as the substituent on the aliphatic hydrocarbon group shown by $R_2$ in the compound of type 2 represented by general formula (A) is synthesized, a compound with hydroxy group protected with a protective group as $R_2$ in the compound of general formula (3) is used. The protective group can be readily removed off as done in the reaction scheme 1 or 2.

In the compound of general formula (3), the compound wherein each of Y and Z independently represents a hydrogen, a hydroxy or a lower alkoxy group, or Y and Z are combined together to form methylenedioxy may be obtained by the process described in Japanese Patent KOKAI No. 5-208959 using as a starting material the compound of general formula (4):

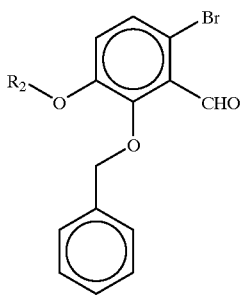

(4)

wherein $R_2$ is a substituted or unsubstituted aliphatic hydrocarbon group other than methyl, in a manner similar to the process for producing the 7-benzyloxy-8-methoxy-benzo[c]phenanthridine derivative of general formula (1) shown in the reaction schemes 1 and 2.

The starting compound of general formula (4) may be obtained in a conventional manner by brominating 2-benzyloxy-3-hydroxybenzaldehyde, which is available by the process described in, e.g., J. C. S. Perkin I, 1221 (1976) and J. Org. Chem., 53, 1708 (1988), and then reacting the reaction mixture with a compound of general formula (5):

$R_2$—$A_1$     (5)

wherein $R_2$ has the same significance as defined in formula (4) and $A_1$ is a leaving group such as a halogen atom, an alkylsulfonyl group, etc., in an organic solvent in the presence or absence of a base.

In general formula (3), the compound wherein Y and Z are combined together to form a phenyl ring, namely, the compound of general formula (6):

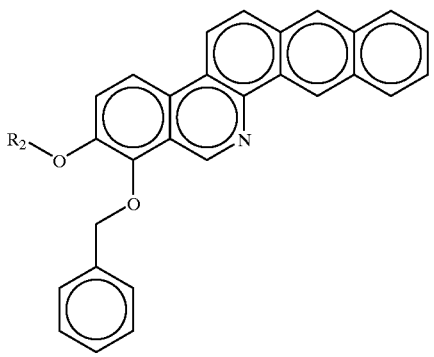

(6)

wherein $R_2$ is a substituted or unsubstituted aliphatic hydrocarbon group other than methyl, may be prepared in a manner similar to the process for producing the 8-benzyloxy-9-methoxy-naphtho[2,3-c]phenanthridine derivative in the reaction scheme 3 described above, except that the compound of general formula (4) is used as the starting compound.

The thus obtained phenanthridinium derivative of the present invention represented by general formula (A) readily releases one equivalent of the acid from its molecule, when treated with a base. It is thus possible to take the following novel structure of phenanthridinium derivative shown by general formula (B) below:

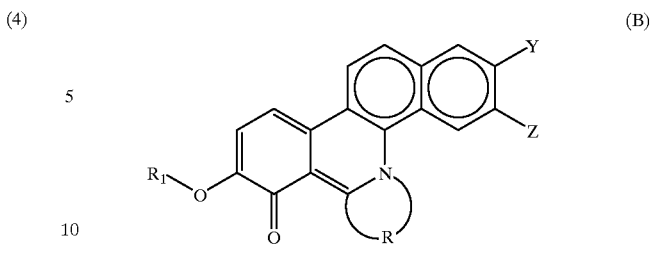

(B)

wherein $R_1$, R, Y and Z have the same significance as defined in general formula (A). Alternatively, the compound of general formula (B) is readily converted into the compound of general formula (A), when treated with an acid.

The compound of general formula (B) is more lipid-soluble than the compound of general formula (A). However, it is considered that the compound of general formula (A) would exert its pharmacological effects in the form of the compound of general formula (B) in vivo to exhibit an antitumor activity. Furthermore, the compound of general formula (B) also plays a role as an intermediate for synthesis of the compound of general formula (A). That is, in the reaction schemes 1 and 2, the compound of general formula (B) is produced after the removal of protection. The acid treatment of the compound of general formula (B) produced after the removal of the protective group gives the compound of general formula (A) in the reaction schemes 1 and 2. Also in the synthesis of the compound of type 2 represented by general formula (A), the corresponding compound of general formula (B) is likewise produced after the removal of the protective group. Similarly, the acid treatment of the compound of general formula (B) gives the compound of general formula (A).

The compound of the present invention is characterized by the chemical and biological characteristics described below.

The phenanthridinium derivatives shown by general formulas (A) and (B) contain the substituted or unsubstituted aliphatic hydrocarbon chain shown by R as a partial structure. It has been found that the cyclic structure serves to steric protection of the site that is considered to be rich in chemical and biological reactivities in known benzo[c]phenanthridinium derivatives, e.g., 2, 3-(methylenedioxy)-5-methyl-7-hydroxy-8-methoxy-benzo[c]phenanthridinium hydrogensulfate (Japanese Patent KOKAI No. 5-208959), and such a feature therefore contributes to improved stability to chemical reduction and biological metabolic reactions.

For example, known 2,3-(methylenedioxy)-5-methyl-7-hydroxy-8-methoxy-benzo[c]phenanthridinium hydrogensulfate is quickly reduced in an aqueous solution at room temperature in the presence of sodium cyanoborohydride as a reducing agent so that the phenanthridinium is lost in a few minutes. In addition, when an in vitro metabolic test using liver homogenate (S9) prepared from human liver was performed with reference to the method described in Arch. Biochem. Biophys., 282, 183 (1990), production of the metabolite was observed. This product coincided with the reduced product formed by the chemical reduction described above.

2,3-(Methylenedioxy)-7-hydroxy-8-methoxy-5,6-propano-benzo[c]phenanthridinium chloride, which is one of the compounds of the present invention, was treated with sodium cyanoborohydride in an aqueous solution at room temperature. When compared to the known 2,3-(methylenedioxy)-5-methyl-7-hydroxy-8-methoxy-benzo[c]phenanthridinium hydrogensulfate above, the compound of the present invention disappears obviously gradually. Furthermore, no metabolite was produced in in vitro metabolic test using liver homogenate (S9) prepared from human liver, demonstrating that the compound of the present invention is resistant to the reductive metabolic reaction. Therefore, the compound of the present invention has an improved stability and hence, is extremely useful as a medicine.

Next, representative examples of the phenanthridinium derivative shown by general formula (A) are given in Table 1. However, the compounds of the present invention are not deemed to be limited thereto.

TABLE 1

| No. | Compound |
|---|---|
| A-1 | 7-hydroxy-8-methoxy-5,6-propano-benzo[c]phenanthridinium salt |
| A-2 | 7-hydroxy-8-methoxy-5,6-(2-hydroxypropano)-benzo[c]phenanthridinium salt |
| A-3 | 2,3-(methylenedioxy)-7-hydroxy-8-methoxy-5,6-ethano-benzo[c]phenanthridinium salt |
| A-4 | 2,3-(methylenedioxy)-7-hydroxy-8-methoxy-5,6-propano-benzo[c]phenanthridinium salt |
| A-5 | 2,3-(methylenedioxy)-7-hydroxy-8-methoxy-5,6-(2-methylpropano)-benzo[c]phenanthridinium salt |
| A-6 | 2,3-(methylenedioxy)-7-hydroxy-8-methoxy-5,6-(2-hydroxypropano)-benzo[c]phenanthridinium salt |
| A-7 | 2,3-(methylenedioxy)-7-hydroxy-8-methoxy-5,6-butano-benzo[c]phenanthridinium salt |
| A-8 | 2,7-dihydroxy-3,8-dimethoxy-5,6-propano-benzo[c]-phenanthridinium salt |
| A-9 | 8-hydroxy-9-methoxy-6,7-propano-naphtho[2,3-c]-phenanthridinium salt |
| A-10 | 8-hydroxy-9-methoxy-6,7-(2-methylpropano)-naphtho[2,3-c]phenanthridinium salt |
| A-11 | 8-hydroxy-9-methoxy-6,7-(2-hydroxypropano)-naphtho[2,3-c]phenanthridinium salt |
| A-12 | 8-hydroxy-9-methoxy-6,7-butano-naphtho[2,3-c]-phenanthridinium salt |
| A-13 | 7-hydroxy-8-(2-hydroxyethoxy)-5,6-propano-benzo[c]phenanthridinium salt |
| A-14 | 2,3-(methylenedioxy)-7-hydroxy-8-allyloxy-5,6-propano-benzo[c]phenanthridinium salt |
| A-15 | 2,3-(methylenedioxy)-7-hydroxy-8-(2-hydroxy-ethoxy)-5,6-propano-benzo[c]phenanthridinium salt |
| A-16 | 2,3-(methylenedioxy)-7-hydroxy-8-(2-methoxy-ethoxy)-5,6-propano-benzo[c]phenanthridinium salt |
| A-17 | 2,3-(methylenedioxy)-7-hydroxy-8-(2-acetoxye-thoxy)-5,6-propano-benzo[c]phenanthridinium salt |
| A-18 | 2,3-(methylenedioxy)-7-hydroxy-8-(carbamoylme-thoxy)-5,6-propano-benzo[c]phenanthridinium salt |
| A-19 | 2,3-(methylenedioxy)-7-hydroxy-8-trifluorome-thoxy-5,6-propano-benzo[c]phenanthridinium salt |
| A-20 | 2,3-(methylenedioxy)-7-hydroxy-8-(2-hydroxye-thoxy)-5,6-(2-methylpropano)-benzo[c]phenanthridinium salt |
| A-21 | 8-hydroxy-9-(2-hydroxyethoxy)-6,7-propano-naphtho[2,3-c]phenanthridinium salt |
| A-22 | 8-hydroxy-9-allyloxy-6,7-propano-naphtho[2,3-c]phenanthridinium salt |
| A-23 | 8-hydroxy-9-(2-methoxyethoxy)-6,7-propano-naphtho[2,3-c]phenanthridinium salt |
| A-24 | 8-hydroxy-9-(2-acetoxyethoxy)-6,7-propano-naphtho[2,3-c]phenanthridinium salt |
| A-25 | 8-hydroxy-9-(carbamoylmethoxy)-6,7-propano-naphtho[2,3-c]phenanthridinium salt |
| A-26 | 8-hydroxy-9-trifluoromethoxy-6,7-propano-naphtho[2,3-c]phenanthridinium salt |

When the phenanthridinium derivative of the present invention represented by general formula (A) or (B) is employed as a medicine, various known methods are applicable to pharmaceutical preparations and method for administration thereof. That is, the phenanthridinium derivative of the present invention may be administered parenterally, orally, intrarectally, etc. The phenanthridinium derivative may take any form suitable for pharmaceutical preparations including injection, powders, granules, tablets, suppositories, etc. When the phenanthridinium derivative is prepared into pharmaceutical compositions, if necessary, various auxiliary agents used for medicines, namely, carriers and other additives, e.g., a stabilizer, a preservative, a soothing agent, an emulsifier, etc. may be employed, unless they adversely affect the active ingredient.

In the pharmaceutical preparations, the content of the phenanthridinium derivative represented by general formula (A) or (B) may vary in a wide range depending upon preparation form but is generally in a range of 0.01 to 100% (by weight), preferably 0.1 to 50% (by weight). The rest consists of carriers and other additives conventionally used for medicines.

A dose of the phenanthridinium derivative represented by general formula (A) or (B) may change depending upon conditions of the patient, etc. but is approximately 50 to 500 mg per day for adult.

As stated above, the phenanthridinium derivatives of the present invention represented by general formula (A) and (B) exhibit an antitumor activity both in vitro and in vivo and are thus be expected as effective for the treatment of cancer.

Hereinafter the processes for producing the phenanthridinium derivatives of the present invention and pharmacological actions as well as pharmaceutical preparations thereof will be described in more detail, by referring to Examples and Test Examples on pharmacological actions. However the present invention is not deemed to be limited only thereto.

EXAMPLE 1

Synthesis of 6-(3-hydroxypropyl)-7-benzyloxy-8-methoxy-benzo[c]phenanthridine

7-Benzyloxy-8-methoxy-benzo[c]phenanthridine (prepared by the process described in Japanese Patent KOKAI No. 5-208959, 284 mg, 0.78 mmol) was suspended in acetonitrile (10 mL), and trifluoroacetic acid (60 μL, 0.78 mmol), 3-bromo-1-propanol (71 μL, 0.79 mmol) and tris (trimethylsilyl)silane (481 μL, 1.56 mmol) were added to the suspension. The mixture was stirred at 80° C. on an oil bath. After the suspension was dissolved, azobis(isobutyronitrile) (256 mg, 1.56 mmol) was added to the solution followed by heating under reflux. An hour later, the reaction mixture was allowed to cool to room temperature, and then a saturated sodium hydrogencarbonate aqueous solution (60 mL) was added thereto followed by extraction with methylene chloride. After the organic layer was washed with saturated sodium chloride aqueous solution and dried over anhydrous sodium sulfate, the solvent was distilled off in vacuo. The residue was passed through a silica gel column (eluted with 1% methanol-methylene chloride). The main fractions were collected and concentrated in vacuo to give 6-(3-hydroxypropyl)-7-benzyloxy-8-methoxy-benzo[c] phenanthridine as a crude product (purity 50%, 142 mg, yield 21%) in a yellow brown dry mass.

FAB-MS(positive mode)m/z:

424([M+H]$^+$), 366([M+H—CH$_3$CH$_2$CH$_2$OH]$^+$), 333 ([M+H-benzyl]$^+$);

$^1$H-NMR(200 MHz, CDCl$_3$)δ:

9.31(1H, m), 8.51(1H, d, J=9.3 Hz), 8.46(1H, d, J=9.3 Hz), 7.95(1H, d, J=9.5 Hz), 7.94(1H, m), 7.77(1H, m), 7.66(1H, m), 7.65(1H, d, J=9.3 Hz), 7.62–7.36(5H, m), 5.23(2H, s), 4.07(3H, s), 3.82(2H, t, J=6.9 Hz), 3.64 (2H, t, J=6.1 Hz), 2.24(2H, tt, J=6.9&6.1 Hz).

EXAMPLE 2

Synthesis of 7-hydroxy-8-methoxy-5,6-propano-benzo[c] phenanthridinium chloride (Compound No. A-1) (X$^-$=Cl$^-$)

The crude product, 6-(3-hydroxypropyl)-7-benzyloxy-8-methoxy-benzo[c]phenanthridine (purity 50%, 120 mg, 0.14 mmol) synthesized in Example 1 was dissolved in methylene chloride (4 mL). Methanesulfonyl chloride (22 μL, 0.28 mmol) and N,N-diisopropylethylamine (50 μL, 0.28 mmol) were added to the solution. The mixture was stirred at room temperature for 20 minutes. After methanol (1 mL) was added to the reaction mixture, the solution was concentrated in vacuo. The residue was passed through a silica gel column (eluted with 8% methanol-methylene chloride). The main fractions were collected, and the solvent was distilled off in vacuo. Acetic acid (1.6 mL) and conc. hydrochloric acid (0.8 mL) were added to the residue to dissolve. The solution was stirred at 60° C. on an oil bath for 20 minutes. After the reaction mixture was cooled to room temperature, a saturated sodium hydrogencarbonate aqueous solution (160 mL) was added thereto, which was then extracted with methylene chloride. The organic layer was washed with water and dried over anhydrous sodium sulfate (containing the compound of general formula (B)). The organic layer was filtered to remove sodium sulfate. A 4M hydrogen chloride-dioxane solution was added to the filtrate until the red purple solution completely turned golden yellow. The solution was concentrated in vacuo. The residue was purified by silica gel column chromatography (eluted with 8–12% methanol-methylene chloride) to give Compound No. A-1 ($X^-=Cl^-$) (29 mg, yield 59%) as golden yellow powders.

FAB-MS(positive mode)m/z:
316($M^+$);
$^1$H-NMR(200 MHz, DMSO-$d_6$)δ:
11.44(1H, brs), 8.93(1H, d, J=9.4 Hz), 8.93(1H, m), 8.61(1H, d, J=9.2 Hz), 8.39(1H, d, J=9.2 Hz), 8.29(1H, m), 8.15(1H, d, J=9.1 Hz), 7.92–7.82(2H, m), 5.57(2H, brt, J=7.2 Hz), 4.23(2H, brt, J=7.6 Hz), 4.10(3H, s), 2.49(2H, m).

EXAMPLE 3

Synthesis of 2,3-(methylenedioxy)-6-(3-hydroxypropyl)-7-benzyloxy-8-methoxy-benzo[c]phenanthridine 2,3-(Methylenedioxy)-7-benzyloxy-8-methoxy-benzo[c]phenanthridine (prepared by the process described in Japanese Patent KOKAI No. 5-208959, 1.228 g, 3.00 mmols) was suspended in acetonitrile (48 mL), and trifluoroacetic acid (231 μL, 3.00 mmols), 3-bromo-1-propanol (271 μL, 3.00 mmols) and tris(trimethylsilyl)silane (1.85 mL, 6.00 mmols) were added to the suspension. The mixture was stirred at 80° C. on an oil bath. After the suspension was dissolved, azobis(isobutyronitrile) (0.985 g, 6.00 mmols) was added to the solution followed by heating under reflux. 90 minutes later, the reaction mixture was cooled to room temperature. By separating the precipitated crystals through filtration, the starting material, 2,3-(methylenedioxy)-7-benzyloxy-8-methoxy-benzo[c]phenanthridine, was recovered as the trifluoroacetate (0.680 g). The filtrate was concentrated in vacuo, and a saturated sodium hydrogencarbonate aqueous solution (40 mL) was added to the residue followed by extraction with methylene chloride (50 mL). After the organic layer was washed with water (50 mL) and dried over anhydrous sodium sulfate, the solvent was distilled off in vacuo. The residue was purified by silica gel column chromatography (eluted with 10% ethyl acetate-toluene) to give 2,3-(methylenedioxy)-6-(3-hydroxypropyl)-7-benzyloxy-8-methoxy-benzo[c]phenanthridine (0.210 g, yield 15%) as light brown powders.

FAB-MS(positive mode)m/z:
468([M+H]$^+$), 377([M+H-benzyl]$^+$);
$^1$H-NMR(200 MHz, CDCl$_3$)δ:
8.65(1H, s), 8.45(1H, d, J=9.3 Hz), 8.31(1H, d, J=9.1 Hz), 7.78(1H, d, J=9.1 Hz), 7.60(1H, d, J=9.3 Hz), 7.57(2H, dd, J=7.9&1.7 Hz), 7.49–7.37(3H, m), 7.24(1H, s), 6.11(2H, s), 5.21(2H, s), 4.06(3H, s), 3.76(2H, t, J=7.0 Hz), 3.61(2H, t, J=6.1 Hz), 2.22(2H, tt, J=7.0&6.1 Hz).

EXAMPLE 4

Synthesis of 2,3-(methylenedioxy)-7-hydroxy-8-methoxy-5,6-propano-benzo[c]phenanthridinium chloride (Compound No. A-4) ($X^-=Cl^-$)

2,3-(Methylenedioxy)-6-(3-hydroxypropyl)-7-benzyloxy-8-methoxy-benzo[c]phenanthridine (192 mg, 0.41 mmol) was dissolved in methylene chloride (8 mL). Methanesulfonyl chloride (41 μL, 0.53 mmol) and N,N-diisopropylethylamine (95 μl, 0.53 mmol) were added to the solution. The mixture was stirred at room temperature for 30 minutes. Methanol (1 mL) was added to the reaction mixture followed by concentration in vacuo to give yellow brown syrup (530 mg). Acetic acid (4 mL) and conc. hydrochloric acid (2 mL) were added to the residue to dissolve. The solution was stirred at 60° C. on an oil bath for 15 minutes. The reaction mixture was cooled to room temperature and then concentrated in vacuo. The residue was dissolved in a 5% methanol-methylene chloride solution (100 mL) and a saturated sodium hydrogencarbonate aqueous solution (80 mL) was added to the solution. The mixture was vigorously agitated until the orange organic layer completely turned red purple. The organic layer was separated and washed with water, and then dried over anhydrous sodium sulfate (containing the compound of general formula (B)). The organic layer was filtered to remove sodium sulfate. A 4M hydrogen chloride-dioxane solution was added to the filtrate until the solution completely turned orange. The solution was concentrated in vacuo. The residue was purified by silica gel column chromatography (eluted with 8–12% methanol-methylene chloride) to give Compound No. A-4 ($X^-=Cl^-$) (112 mg, yield 69%) as golden yellow powders.

FAB-MS(positive mode)mn/z:
360($M^+$);
UV$\lambda_{max}$ nm:
(in 1M HCl) 438, 342, 320, 271, (in pH9) 488, 347, 335, 278;
$^1$H-NMR(200 MHz, DMSO-$d_6$)δ:
8.72(1H, d, J=9.2 Hz), 8.43(1H, d, J=9.2 Hz), 8.24(1H, s), 8.19(1H, d, J=9.2 Hz), 8.03(1H, d, J=9.2 Hz), 7.71(1H, s), 6.33(2H, s), 5.47(2H, brt, J=7.1 Hz), 4.16(2H, brt, J=7.7 Hz), 4.06(3H, s), 2.44(2H, m).

EXAMPLE 5

Synthesis of 2,3-(methylenedioxy)-5-methyl-6-ethoxy-7-benzyloxy-8-methoxy-5,6-dihydrobenzo[c]phenanthridine 2,3-(Methylenedioxy)-7-benzyloxy-8-methoxy-benzo[c]phenanthridine (prepared by the process described in Japanese Patent KOKAI No. 5-208959, 4.487 g, 10.96 mmols) and methyl 2-nitrobenzenesulfonate (4.30 g, 19.79 mmols) were dissolved in toluene (90 mL). The solution was stirred for 24 hours while heating at 110° C. After the reaction mixture was cooled to room temperature, the precipitated crystals were separated by filtration, and then washed with toluene. The crystals were suspended in N,N-dimethylformamide (62 mL), and pyridine (0.62 mL) was added to the suspension. The mixture was stirred at 60° C. for 2 hours. After the mixture was cooled to room temperature, the crystals were taken by filtration and washed successively with toluene and hexane. The thus obtained golden yellow crystals were suspended in ethanol (124 mL) and, 0.1N sodium hydroxide aqueous solution (93 mL) was added to the suspension. The mixture was stirred until the golden yellow color was completely lost. The resulting light brown crystals were taken by filtration and washed with 50% ethanolic water to give 2,3-(methylenedioxy)-5-methyl-6-ethoxy-7-benzyloxy-8-methoxy-5,6-dihydrobenzo[c]phenanthridine (3.016 g, yield 59%) as light brown powders.

FAB-MS(positive mode)m/z:
424([M—CH$_3$CH$_2$O]$^+$);
$^1$H-NMR(200 MHZ, CDCl$_3$)δ:
7.78(1H, d, J=8.6 Hz), 7.64(1H, d, J=8.6 Hz), 7.63(1H, s), 7.46(1H, d, J=8.6 Hz), 7.58–7.33(5H, m), 7.11(1H, s), 7.06(1H, d, J=8.6 Hz), 6.04(2H, s), 5.64(1H, s), 5.21 (1H, d, J=10.9 Hz), 5.09(1H, d, J=10.9 Hz), 3.94(3H, s), 3.90(1H, dq, J=9.6&7.1 Hz), 3.60(1H, dq, J=9.6&7.1 Hz), 2.61(3H, s), 1.05(3H, t, J=7.1 Hz).

EXAMPLE 6

Synthesis of 2,3-(methylenedioxy)-5-methyl-6-[3-(t-butyldimethylsiloxy)propyl]-7-benzyloxy-8-methoxy-5,6-dihydrobenzo[c]phenanthridine In a dry flask, a piece of magnesium (0.468 g, 19.3 mmols) was charged, and tetrahydrofuran (15 mL) was added thereto. A solution of 3-(t-butyldimethylsiloxy)propyl bromide (2.36 g, 9.63 mmols) in tetrahydrofuran (15 mL), iodine (a few pieces) and 1,2-dibromoethane (a few drops) were added portionwise to the mixture. The resulting mixture was stirred at room temperature for an hour. A solution of 2,3-(methylenedioxy)-5-methyl-6-ethoxy-7-benzyloxy-8-methoxy-5,6-dihydrobenzo[c]phenanthridine (1.01 g, 2,2 mmols) in tetrahydrofuran (10 mL) was added to the resulting solution followed by stirring at room temperature for 2 hours. A saturated ammonium chloride aqueous solution was added to the reaction mixture followed by extracting with ethyl acetate. The organic layer was separated, washed with saturated sodium chloride aqueous solution and then dried over anhydrous sodium sulfate. After sodium sulfate was removed by filtration, the solvent was distilled off in vacuo. The resulting residue was purified by silica gel column chromatography (eluted with 33–66% methylene chloride-hexane) to give 2,3-(methylenedioxy)-5-methyl-6-[3-(t-butyldimethylsiloxy)propyl]-7-benzyloxy-8-methoxy-5,6-dihydrobenzo[c]phenanthridine (1.12 g, yield 96%) as colorless amorphous solid.

$^1$H-NMR(200 MHz, CDCl$_3$)δ:
7.69(1H, d, J=8.6 Hz), 7.64(1H, s), 7.57–7.35(7H, m), 7.09(1H, s), 6.96(1H, d, J=8.6 Hz), 6.05–6.02(2H, m), 5.17(1H, d, J=11.4 Hz), 5.09(1H, d, J=11.4 Hz), 4.29 (1H, dd, J=9.5&5.1 Hz), 3.96(3H, s), 3.45(2H, t, J—6.8 Hz), 2.41(3H, s), 1.80–1.53(2H, m), 1.40–1.20(2H, m), 0.77(9H, s), −0.07(3H, s), −0.09(3H, s).

EXAMPLE 7

Synthesis of 2,3-(methylenedioxy)-6-[3-(t-butyldimethylsiloxy)propyl]-7-benzyloxy-8-methoxy-benzo[c]phenanthridine After 2,3-(methylenedioxy)-5-methyl-6-[3-(t-butyldimethylsiloxy)propyl]-7-benzyloxy-8-methoxy-5,6-dihydrobenzo[c]phenanthridine (871 mg, 1.46 mmol) was dissolved in toluene (30 mL), activated manganese dioxide (4.36 g) was added to the solution. The mixture was stirred at 100° C. for 2 hours. Manganese dioxide was removed by filtration. Thereafter, the filtrate was concentrated in vacuo. The resulting residue was purified by silica gel column chromatography (eluted with 33–66% methylene chloride-hexane) to provide 2,3-(methylenedioxy)-6-[3-(t-butyldimethylsiloxy)propyl]-7-benzyloxy-8-methoxy-benzo[c]phenanthridine (457 mg, yield 54%) as colorless powders.

FAB-MS(positive mode)m/z:
582([M+H]$^+$);
$^1$H-NMR(200 MHz, CDCl$_3$)δ:
8.73(1H, s), 8.40(1H, d, J=9.4 Hz), 8.28(1H, d, J=9.2 Hz), 7.75(1H, d, J=8.8 Hz), 7.60–7.50(3H, m), 7.47–7.35 (3H, m), 7.22(1H, s), 6.11(2H, s), 5.16(2H, s), 4.02(3H, s), 3.75–3.63(4H, m), 2.32–2.18(2H, m), 0.77(9H, s), 0.02(6H, s).

EXAMPLE 8

Synthesis of 2,3-(methylenedioxy)-6-(3-hydroxypropyl)-7-benzyloxy-8-methoxy-benzo[c]phenanthridine After 2,3-(methylenedioxy)-6-[3-(t-butyldimethylsiloxy) propyl]-7-benzyloxy-8-methoxy-benzo[c]phenanthridine (374.4 mg, 0.644 mmol) was dissolved in tetrahydrofuran (3.2 mL), tetrabutylammonium fluoride (1M tetrahydrofuran solution, 1.9 mL) was added to the solution. The mixture was stirred overnight at room temperature. Water was added to the reaction mixture followed by extraction with methylene chloride. The organic phase was dried over anhydrous sodium sulfate and then concentrated in vacuo. The resulting residue was purified by silica gel column chromatography (eluted with methylene chloride) to provide 2,3-(methylenedioxy)-6-(3-hydroxypropyl)-7-benzyloxy-8-methoxy-benzo[c]phenanthridine (263.7 mg, yield 88%) as colorless powders.

The data, measured by the analytical instrument, of this product coincided with those of the product synthesized in Example 3.

EXAMPLE 9

Synthesis of 2,3-(methylenedioxy)-5-methyl-6-[4-(t-butyldimethylsiloxy)butyl]-7-benzyloxy-8-methoxy-5,6-dihydrobenzo[c]phenanthridine 2,3-(Methylenedioxy)-5-methyl-6-[4-(t-butyldimethylsiloxy)butyl]-7-benzyloxy-8-methoxy-5,6-dihydrobenzo[c]phenanthridine was obtained (yield 80%) as colorless amorphous solid in a manner similar to Example 8 except that 4-(t-butyldimethylsiloxy)butyl chloride was employed in place of 3-(t-butyldimethylsiloxy)propyl bromide in Example 6.

$^1$H-NMR(200 MHz, CDCl$_3$)δ:
7.70(1H, d, J=8.7 Hz), 7.63(1H, s), 7.54(1H, d, J=8.5 Hz), 7.54–7.32(6H, m), 7.09(1H, s), 6.96(1H, d, J=8.6 Hz), 6.04–6.02(2H, m), 5.17(1H, d, J=11.3 Hz), 5.09(1H, d, J=11.3 Hz), 4.29(1H, dd, J=7.3&6.5 Hz), 3.96(3H, s), 3.48(2H, dd, J=5.9&5.4 Hz), 2.41(3H, s), 1.56–1.26 (2H, m), 0.87–0.83(9H, m), 0.04~−0.04(6H, m).

EXAMPLE 10

Synthesis of 2,3-(methylenedioxy)-6-[4-(t-butyldimethylsiloxy)butyl]-7-benzyloxy-8-methoxy-benzo[c]phenanthridine After 2,3-(methylenedioxy)-5-methyl-6-[4-(t-butyldimethylsiloxy)butyl]-7-benzyloxy-8-methoxy-5,6-dihydrobenzo[c]phenanthridine (300 mg, 0.49 mmol) was dissolved in toluene (8 mL), activated manganese dioxide (1.5 g) was added to the solution. The mixture was heated to reflux for an hour. After cooling to room temperature, the reaction mixture was diluted with a 10% methanol-methylene chloride solution (12 mL) followed by filtration. The filtrate was concentrated in vacuo. The resulting residue was purified by silica gel column chromatography (eluted with methylene chloride) to provide 2,3-(methylenedioxy)-6-[4-(t-butyldimethylsiloxy)butyl]-7-benzyloxy-8-methoxy-benzo[c]phenanthridine (205 mg, yield 70%) as light brown crystals.

FAB-MS(positive mode)m/z:
596([M+H]$^+$);
$^1$H-NMR(200 MHz, CDCl$_3$)δ:
8.74(1H, s), 8.44(1H, d, J=9.4 Hz), 8.31(1H, d, J=9.1 Hz), 7.77(1H, d, J=8.8 Hz), 7.58(1H, d, J=9.0 Hz), 7.60–7.55(2H, m), 7.47–7.35(3H, m), 7.24(1H, s), 6.11 (2H, s), 5.17(2H, s), 4.04(3H, s), 3.64(4H, m), 2.01(2H, m), 1.58(2H, m), 0.88(9H, m), 0.04(6H, m).

EXAMPLE 11

Synthesis of 2,3-(methylenedioxy)-6-(4-hydroxybutyl)-7-benzyloxy-8-methoxy-benzo[c]phenanthridine After 2,3-(methylenedioxy)-6-[4-(t-butyldimethylsiloxy)butyl]-7-benzyloxy-8-methoxy-benzo[c]phenanthridine (532 mg, 0.89 mmol) was dissolved in tetrahydrofuran (6 mL), acetic acid (102 μL, 1.78 mmol) and tetrabutylammonium fluoride (1M tetrahydrofuran solution, 1.78 mL) were added to the solution. The mixture was stirred at room temperature. The reaction solution was concentrated in vacuo. The residue was diluted with methylene chloride (30 mL), which was then washed with water. After the organic phase was dried over anhydrous sodium sulfate, the solvent was distilled off in vacuo. The residue was purified by silica gel column chromatography (eluted with 1% methanol-methylene chloride) to give 2,3-(methylenedioxy)-6-(4-hydroxybutyl)-7-benzyloxy-8-methoxy-benzo[c]phenanthridine (372 mg, yield 87%) as light yellow needles.

FAB-MS(positive mode)m/z:
482([M+H]$^+$);
$^1$H-NMR(200 MHz, CDCl$_3$)δ:
8.71(1H, s), 8.45(1H, d, J=9.3 Hz), 8.31(1H, d, J=9.0 Hz), 7.77(1H, d, J=9.0 Hz), 7.59(1H, d, J=9.3 Hz), 7.61–7.55(2H, m), 7.49–7.37(3H, m), 7.24(1H, s), 6.11 (2H, s), 5.17(2H, s), 4.06(3H, s), 3.65(2H, dd, J=7.8&7.2 Hz), 3.59(2H, t, J=6.5 Hz), 2.02(2H, m), 1.64–1.50(2H, m).

EXAMPLE 12

Synthesis of 2,3-(methylenedioxy)-7-hydroxy-8-methoxy-5,6-butano-benzo[c]phenanthridinium chloride (Compound No. A-7) (X$^-$=Cl$^-$)

2,3-(Methylenedioxy)-6-(3-hydroxybutyl)-7-benzyloxy-8-methoxy-benzo[c]phenanthridine (252 mg, 0.52 mmol) was dissolved in methylene chloride (10 mL). Methanesulfonyl chloride (80 μL, 1.03 mmol) and N,N-diisopropylethylamine (186 μl, 1.04 mmol) were added to the solution. The mixture was stirred at room temperature for 20 minutes. After water (30 mL) was added to the reaction mixture, the mixture was extracted with methylene chloride (30 mL). The organic phase was washed successively with saturated sodium hydrogencarbonate aqueous solution and saturated sodium chloride aqueous solution, and then dried over anhydrous sodium sulfate. The solvent was distilled off in vacuo. The residue was purified by silica gel column chromatography (eluted with 0–0.5% methanol-methylene chloride) to give the methanesulfonate (210 mg, yield 72%).

The methanesulfonate (186 mg, 0.33 mmol) was dissolved in toluene (12 mL). The solution was heated to reflux for 2 days. The reaction mixture was concentrated in vacuo. Acetic acid (3 mL) and conc. hydrochloric acid (1.5 mL) were added to the residue. The mixture was stirred at 60° C. for 30 minutes. The reaction mixture was cooled to room temperature and then concentrated in vacuo. The residue was dissolved in a methylene chloride solution (50 mL) and a saturated sodium hydrogencarbonate aqueous solution (50 mL) was added to the solution. The mixture was vigorously agitated until the orange organic layer completely turned red purple. The organic layer was separated (containing the compound of general formula (B)), and washed with water. Methanol (10 mL) and 1M hydrochloric acid aqueous solution (1 mL) were added to the organic phase. The resulting solution was agitated (the solution again turned orange). The solution was concentrated in vacuo. The residue was purified by silica gel column chromatography (eluted with 8% methanol-methylene chloride) to give Compound No. A-7 (X$^-$=Cl$^-$) (86 mg, yield 64%) as orange powders.

FAB-MS(positive mode)m/z:
374(M$^+$);
UVλ$^{max}$ nm:
(in 1M HCl) 446, 345, 325, 275, (in pH9) 495, 353, 335, 283;
$^1$H-NMR(200 MHz, DMSO-d$_6$)δ:
11.41(1H, brs), 8.66(1H, d, J=9.2 Hz), 8.47(1H, d, J=9.2 Hz), 8.19(1H, d, J=8.8 Hz), 8.05(1H, d, J=9.0 Hz), 7.90(1H, s), 7.70(1H, s), 6.31(2H, s), 5.11(2H, m), 4.26(2H, m), 4.08(3H, s), 2.05–1.87(2H, m), 1.85–1.67 (2H, m).

EXAMPLE 13

Synthesis of N-((2'-benzyloxy)-3'-methoxy-6'-bromobenzyl)-1-anthrylamine

2-Benzyloxy-3-methoxy-6-bromobenzaldehyde (8.32 g, 23.2 mmols) prepared by the process described in J.C.S. Perkin I, 1221 (1976) and J. Org. Chem., 53, 1708 (1988) and 1-aminoanthracene (manufactured by ALDRICH, 90%, 5.00 g, 23.3 mmols) were dissolved in toluene (230 mL). While vigorously stirring, the solution was heated to reflux at 120° C. for 2 hours. With still heating at 120° C., toluene (180 mL) was gradually added to the reaction mixture over 3 hours and at the same time, the solvent was distilled off. After cooling to ambient temperature, toluene (70 mL) was added to the mixture. Under chilling with water, dimethylamine-borane complex (1.03 g, 17.5 mmols) and acetic acid (30 mL) were added to the resulting mixture in succession. After stirring at room temperature for 75 minutes, 1M hydrochloric acid aqueous solution (130 mL) was added to the mixture while chilling with water. The reaction mixture was filtered. The filtrate was separated into the organic phase and the aqueous phase. The aqueous phase was extracted with toluene (200 mL×2) and the fraction was combined with the organic phase previously obtained. The combined mixture was dried over anhydrous sodium sulfate. The solvent was distilled off in vacuo. The residue was purified by silica gel column chromatography (eluted with 10% ethyl acetate-hexane) to give N-((2'-benzyloxy)-3'-methoxy-6'-bromobenzyl)-1-anthrylamine (12.77 g, quantitative yield) as yellow powders.

$^1$H-NMR(200 MHz, DMSO-d$_6$)δ:
8.86(1H, s), 8.38(1H, s), 7.98(2H, m), 7.50–7.07(10H, m), 6.57(1H, m), 6.20(1H, t, J=4.5 Hz), 5.05(2H, s), 4.47(1H, s), 4.44(1H, s), 3.90(3H, s).

EXAMPLE 14

Synthesis of 8-benzyloxy-9-methoxy-naphtho[2,3-c] phenanthridine

After N-((2'-benzyloxy)-3'-methoxy-6'-bromobenzyl)-1-anthrylamine (10.81 g, 21.70 mmols) was dissolved in toluene (1 L), trioctyltin hydride (19.95 g, 43.43 mmols) was added to the solution and the temperature was elevated to 105° C. Subsequently, 2,2'-azobis(2-methylbutyronitrile) (8.36 g, 43.46 mmols) was added to the mixture. The solution was heated to reflux for 2 hours at 120° C. After cooling to room temperature, activated manganese dioxide (10.81 g) was added to the resulting mixture. The mixture was stirred for 30 minutes. After ethanol (200 mL) was added thereto, the reaction solution was filtered to remove manganese dioxide. The filtrate was concentrated in vacuo. The resulting residue was crystallized from hexane-methylene chloride solvent mixture to provide 8-benzyloxy-9-methoxy-naphtho[2,3-c]phenanthridine (4.04 g, yield 45%) as light yellow powders.

FAB-MS(positive mode)m/z:
416([M+H]$^+$);
$^1$H-NMR(200 MHz, DMSO-d$_6$)δ:
9.82(1H, s), 9.65(1H, s), 8.67(3H, m), 8.37–8.15(3H, m), 7.94(1H, d, J=9.3 Hz), 7.60(4H, m), 7.40(3H, m), 5.35(2H, s), 4.10(3H, s).

EXAMPLE 15

Synthesis of 8-hydroxy-9-methoxy-6,7-propano-naphtho[2,3-c]phenanthridinium chloride (Compound No. A-9) (X$^-$=Cl$^-$)

8-Benzyloxy-9-methoxy-naphtho[2,3 -c]phenanthridine (231 mg, 0.56 mmol) was suspended in acetonitrile (80 mL), and trifluoroacetic acid (43 μL, 0.56 mmol), 3-bromo-1-propanol (51 μL, 0.56 mmol) and tris(trimethylsilyl)silane (346 μL, 1.12 mmol) were added to the suspension. The mixture was stirred at 80° C. on an oil bath. After the suspended matter was dissolved, azobis(isobutyronitrile) (184 mg, 1.12 mmol) was added to the solution followed by heating under reflux. An hour later, the reaction mixture was cooled to room temperature. Saturated sodium hydrogencarbonate aqueous solution (50 mL) was added to the residue followed by extraction with methylene chloride. After the organic layer was washed with water and dried over anhydrous sodium sulfate, the solvent was distilled off in vacuo. The residue was passed through a silica gel column (eluted with 1% methanol-methylene chloride). The main fractions were collected and the solvent was distilled off in vacuo. The residue was dissolved in toluene (3 mL) and activated manganese dioxide (100 mg) was added to the solution. The mixture was stirred at room temperature for 90 minutes. Manganese dioxide was filtered off and the filtrate was concentrated in vacuo to provide crude 7-(3-hydroxypropyl)-8-benzyloxy-9-methoxy-naphtho[2,3-c] phenanthridine (83 mg) as brown dry mass.

The crude product was dissolved in methylene chloride (3 mL). Methanesulfonyl chloride (13 μL, 0.17 mol) and N,N-diisopropylethylamine (30 μL, 0.17 mmol) were added to the solution. The mixture was stirred at room temperature for 45 minutes. After methanol (1 mL) was added to the reaction mixture, the mixture was concentrated in vacuo to give a dry yellow brown syrup-like mass. Acetic acid (1.2 mL) and conc. hydrochloric acid (0.6 mL) were added to the mass to dissolve. The solution was stirred at 60° C. for 25 minutes on an oil bath. The reaction solution was then cooled to room temperature and saturated sodium hydrogencarbonate aqueous solution (100 mL) was added thereto. The mixture was then extracted with methylene chloride. The organic phase was separated and washed with water, and then dried over anhydrous sodium sulfate (which contained the compound of general formula (B)). Sodium sulfate was filtered off and a 4M hydrogen chloride-dioxane solution was added to the solution until the solution completely turned orange. The solution was concentrated in vacuo. The residue was purified by silica gel column chromatography (eluted with 8–12% methanol-methylene chloride) and then by Sephadex LH-20 gel filtration chromatography (eluted with 20% methanol-5 mM hydrochloric acid aqueous solution) to give Compound No. A-9 (X$^-$=Cl$^-$) (10 mg, yield 4%) as golden yellow powders.

FAB-MS(positive mode)m/z:
366(M$^+$);
$^1$H-NMR(200 MHz, DMSO-d$_6$)δ:
11.43(1H, brs), 9.56(1H, s), 8.88(1H, s), 8.81(1H, d, J=9.5 Hz), 8.61(1H, d, J=9.2 Hz), 8.47(1H, d, J=9.2 Hz), 8.46(1H, m), 8.24(1H, m), 8.17(1H, d, J=9.2 Hz), 7.80–7.72(2H, m), 5.77(2H, brt, J=7.1 Hz), 4.28(2H, brt, J=7.7 Hz), 4.11(3H, s), 2.51(2H, m).

Pharmacological Test Examples

The compounds of the present invention were examined on the antitumor activity, and the thus obtained results are shown below. The phenanthridinium derivatives represented by general formula (A) prevented the growth of tumor cells, as demonstrated below.

1. Growth prevention against cancer cells

Human uterus cancer-derived cells HeLa S3 were incubated at 37° C. for 24 hours in 5% CO$_2$. A test compound was then brought into contact with the cells for 72 hours. Then, the cells were stained with 0.05% Methylene Blue. The pigment was extracted from the stained cells. The growth inhibition of the cells were determined based on absorbance at 660 nm to calculate 50% growth inhibitory concentration (IC$_{50}$). The results are shown in Table 2.

TABLE 2

| Compound No. | 50% Inhibitory Concentration (IC$_{50}$) (μM) |
| --- | --- |
| A-4 (X$^-$ = Cl$^-$) | 0.17 |
| A-7 (X$^-$ = Cl$^-$) | 5.6 |

2. Antitumor effect on cancer cells in vivo

Mouse leukemia cells P388 was intravenously injected to female CDF1 mice of 6 weeks old in a dose of 10$^5$ cells/mouse. A 5% glucose aqueous solution of 2,3-(methylenedioxy)-7-hydroxy-8-methoxy-5,6-propano-benzo[c]phenanthridinium chloride (Compound No. A-4 of the present invention, (X$^-$=Cl$^-$)) was intravenously injected by single administration on the day following the tumor transportation. The antitumor effect was evaluated by comparing the ratio (T/C %) of survival days to the median of survival days in the control group (5 mice). The results are shown in Table 3.

TABLE 3

| Compound No. | Dose (mg/kg/day) | Survived Days (day) | Effect (T/C %) |
| --- | --- | --- | --- |
| A-4 (X$^-$ = Cl$^-$) | 100 | >30 | >357 |
|  | 75 | >30 | >357 |
|  | 50 | 21 | 250 |
|  | 25 | 14 | 167 |
| Control group* | — | 8.4 | 100 |

*Physiological saline was given.

3. Acute Toxicity

The acute toxicity was assessed by intravenous injection of 2,3-(methylenedioxy)-7-hydroxy-8-methoxy-5,6-propano-benzo[c]phenanthridinium chloride (Compound No. A-4 of the present invention, (X$^-$=Cl$^-$)) to female CDF1 mice of 6 weeks old. The animal survived even in a dose of 100 mg/kg, without showing any death.

EXAMPLE 16

Pharmaceutical preparations

After weighing 1 g of 2,3-(methylenedioxy)-7-hydroxy-8-methoxy-5,6-propano-benzo[c]phenanthridinium chloride (Compound No. A-4 of the present invention, X$^-$ Cl$^-$), 1 g of polysorbate and 1 g of Macrogol 400, these compounds are dispersed and dissolved in 100 g of sterile water for injection. The solution is filtered through a membrane filter. The filtrate is dispensed in each ampoule and freeze-dried in a conventional manner to provide an injection preparation containing 50 mg/ampoule of Compound No. A-4 ($X^-=Cl^-$).

EXAMPLE 17

Chemical reduction

The compound of the present invention (0.1 mg/mL aqueous solution, 0.1 mL) was diluted with methanol (1.0 mL). An aqueous solution of sodium cyanoborohydride (4 mg/mL, 0.02 mL) was added to the solution. The mixture was allowed to stand at room temperature. The reaction was terminated by adding 1% aqueous phosphoric acid (1 mL) thereto. The residual amount of the compound was determined by high performance liquid chromatography. As a control, 2,3-(methylenedioxy)-5-methyl-7-hydroxy-8-methoxy-benzo[c]phenanthridinium hydrogensulfate was similarly reacted. The results are shown in Table 4.

TABLE 4

| Compound No. | Amount of Compound remained after Reduction |
|---|---|
| A-4 ($X^-$ = $Cl^-$) | 50 |
| A-7 ($X^-$ = $Cl^-$) | 100 |
| Control | 0 |

Industrial Applicability

The phenanthridinium derivative of the present invention exhibits an antitumor activity, is resistant to chemical reduction and biological metabolic reactions and thus extremely effective as a medicine.

What is claimed is:

1. A novel phenanthridinium derivative compound represented by general formula (A):

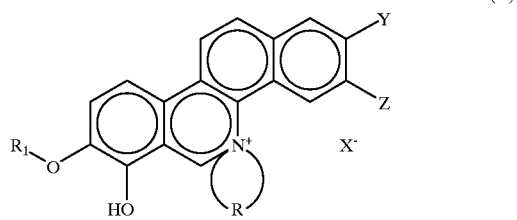

(A)

wherein $R_1$ is a substituted or unsubstituted lower aliphatic hydrocarbon group;

R is an aliphatic hydrocarbon chain having 2 to 6 carbon atoms which may optionally be substituted with a substituent selected from the group consisting of a lower alkyl group, a halogen and a hydroxy group;

each of Y and Z independently represents a hydrogen, a hydroxy or a lower alkoxy group; or Y and Z are combined together to form methylenedioxy or a phenyl ring; and, $X^-$ is an acid residue or a hydroacid residue.

2. A novel phenanthridinium derivative compound represented by general formula (B):

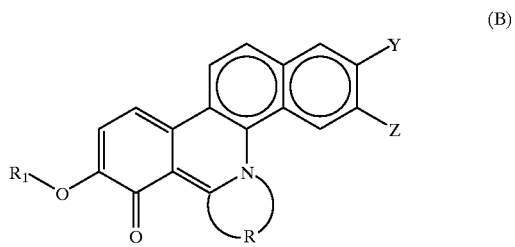

(B)

wherein $R_1$ is a substituted or unsubstituted lower aliphatic hydrocarbon group;

R is a lower aliphatic hydrocarbon chain having 2 to 6 carbon atoms which may optionally be substituted with a substituent selected from the group consisting of a lower alkyl group, a halogen and a hydroxy group;

each of Y and Z independently represents a hydrogen, a hydroxy or a lower alkoxy group; or Y and Z are combined together to form methylenedioxy or a phenyl ring.

3. A compound according to claim 1 or 2, wherein $R_1$ is methyl, ethyl, allyl, 2-hydroxyethyl, 2-methoxyethyl, 2-acetoxyethyl, carbamoylmethyl or trifluoromethyl; R is an unsubstituted polymethylene chain having 3 to 4 carbon atoms; and Y and Z are combined together to form methylenedioxy or a phenyl ring.

4. A 2,3-(methylenedioxy)-7-hydroxy-8-methoxy-5,6-propano-benzo[c]phenanthridinium salt.

5. A pharmaceutical composition comprising a compound according to claim 1 or 2 as an active ingredient, together with a pharmacologically acceptable carrier.

6. A pharmaceutical composition according to claim 5, in an amount effective for the treatment of tumor.

7. A method for treating tumor which comprises administering to human a compound according to claim 1 or 2 at an effectie dose.

* * * * *

UNITED STATES PATENT AND TRADEMARK OFFICE
CERTIFICATE OF CORRECTION

PATENT NO. : 6,187,783 B1
DATED : February 13, 2001
INVENTOR(S) : Akira Masuda, et al.

Page 1 of 1

It is certified that error appears in the above-identified patent and that said Letters Patent is hereby corrected as shown below:

Abstract,
Columns 1 and 23, claim 1,
Please replace formula (A) with the following corrected Formula (A):

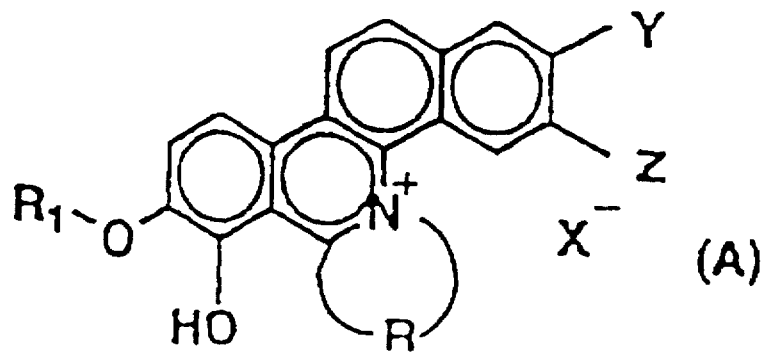

Signed and Sealed this

Ninth Day of October, 2001

Attest:

NICHOLAS P. GODICI
Attesting Officer
Acting Director of the United States Patent and Trademark Office